US006387039B1

(12) United States Patent
Moses

(10) Patent No.: US 6,387,039 B1
(45) Date of Patent: May 14, 2002

(54) IMPLANTABLE HEARING AID

(75) Inventor: Ron L. Moses, 4920 Mimosa, Bellaire, TX (US) 77401

(73) Assignee: Ron L. Moses, Bellaire, TX (US)

( * ) Notice: Subject to any disclaimer, the term of this patent is extended or adjusted under 35 U.S.C. 154(b) by 0 days.

(21) Appl. No.: 09/499,337

(22) Filed: Feb. 4, 2000

(51) Int. Cl.[7] .......................... H04R 25/00; A61N 1/08
(52) U.S. Cl. .......................................... 600/25; 607/57
(58) Field of Search .......................... 600/25; 604/285; 607/57; 623/10

(56) References Cited

U.S. PATENT DOCUMENTS

| | | | | |
|---|---|---|---|---|
| 2,959,645 A | | 11/1960 | Ladd | 179/107 |
| 3,557,775 A | * | 1/1971 | Mahoney | 600/25 |
| 3,764,748 A | * | 10/1973 | Branch et al. | 607/57 |
| 4,520,236 A | | 5/1985 | Gauthier | 179/107 |
| 4,729,366 A | * | 3/1988 | Schaefer | 600/25 |
| 4,756,312 A | | 7/1988 | Epley | 128/420.5 |
| 4,957,478 A | | 9/1990 | Maniglia | 600/25 |
| 5,012,520 A | | 4/1991 | Steeger | 381/68 |
| 5,202,927 A | | 4/1993 | Tøpholm | 381/68 |
| 5,220,918 A | | 6/1993 | Heide et al. | 128/420.6 |
| 5,259,032 A | | 11/1993 | Perkins et al. | 381/68 |
| 5,381,484 A | | 1/1995 | Claes et al. | 381/68.6 |
| 5,390,254 A | | 2/1995 | Adelman | 381/68 |
| 5,425,104 A | | 6/1995 | Shennib | 381/68 |
| 5,535,282 A | | 7/1996 | Luca | 381/68.6 |
| 5,717,771 A | | 2/1998 | Sauer et al. | 381/68.6 |
| 5,796,848 A | | 8/1998 | Martin | 381/68.2 |
| 5,812,680 A | | 9/1998 | Glendon | 381/69 |
| 5,848,171 A | | 12/1998 | Stockham, Jr. et al. | 381/321 |
| D405,528 S | | 2/1999 | Shennib et al. | D24/174 |
| 5,920,635 A | | 7/1999 | Lenz | 381/328 |
| 5,979,589 A | | 11/1999 | Aceti | 181/135 |
| 6,027,532 A | * | 2/2000 | Hobeika | 623/10 |
| 6,042,574 A | * | 3/2000 | O'Halloran | 604/285 |

FOREIGN PATENT DOCUMENTS

| | | | |
|---|---|---|---|
| EP | 0 369 624 | 5/1990 | H04R/25/02 |
| FR | 2 365 267 | 1/1978 | H04R/25/02 |

* cited by examiner

*Primary Examiner*—Eric F. Winakur
*Assistant Examiner*—Nikita R Veniaminov
(74) *Attorney, Agent, or Firm*—Moser, Patterson & Sheridan, L.L.P.

(57) ABSTRACT

The present invention provides an apparatus and method for inserting a relatively compact hearing aid at least partially through the tympanic membrane using a simplified surgical procedure. The hearing aid includes a microphone, an amplifier, and at least one speaker that can be assembled into a single enclosure for insertion through the tympanic membrane. The simplified surgical procedure can be performed on an outpatient basis and generally includes anesthetizing a portion of the tympanic membrane, forming an incision with a cutting instrument in the tympanic membrane and inserting the hearing aid at least partially therethrough. Incisions and placement of a tube in an tympanic membrane for car drainage is routinely performed in pediatric patients and combines low morbidity and good patient tolerability. The tympanic membrane restrains the hearing aid in position for at least a period of time. A power source, such as a battery, powers the hearing aid. Further, a receiver may be included with the hearing aid and can control the hearing aid from external sources. The receiver can control the amplified volume, receive sound transmissions from the opposite ear or a hearing aid in the opposite ear or receive personal communications.

27 Claims, 3 Drawing Sheets

IMPLANTABLE HEARING AID

BACKGROUND OF THE INVENTION

1. Field of the Invention

The present invention relates to assistive hearing devices. More specifically, the present invention relates to a hearing aid mounted internally to an ear.

2. Background of the Related Art

Hearing devices are well known and typically include a microphone, an amplifier and a speaker. Typically, the microphone receives a sound wave and converts the wave into an electrical signal, the amplifier amplifies the electrical signal, and the speaker converts the amplified signal into amplified sound waves that impart vibrations to the tympanic membrane or ear drum in the ear. Common hearing aids are mounted outside the ear canal, particularly around the outer ear. The externally mounted hearing aid has the advantage of accessibility to change batteries and to adjust the volume of sound. However, many users find such externally mounted hearing aides relatively bulky and objectionable for cosmetic reasons.

An alternative to externally mounted hearing aides are internally mounted hearing aids disposed in an ear canal of a user. Such internally mounted hearing aides offer better cosmetic appearance, but have disadvantages as well. For instance, the typical internally mounted hearing aid blocks the majority, if not all, of the ear canal diameter. Such blockage can cause the body of the user to produce an excessive amount of ear wax in the ear canal and can cause ear infections. Further, the blocking of the ear canal obstructs the natural transmission of sound waves through the ear canal that impact the tympanic membrane. Unless a user is totally hearing impaired, any ability of the tympanic membrane to register the natural occurring sound waves is reduced or eliminated. Thus, the user is substantially dependent upon the sound fidelity of the hearing aid. Still further, the typical internally mounted hearing aids may still be visible in the ear canal by peering at the head of the user from the side.

Some hearing systems deliver audio information to the ear through electromagnetic transducers. A microphone and amplifier transmit an electronic signal to a transducer that converts the electronic signal into vibrations. The vibrations vibrate the tympanic membrane or parts of the middle ear that transmits the sound impulses without reconverting to audio sound waves from a speaker. A separate magnet can be remotely mounted at or near the tympanic membrane. The interaction between the magnetic fields of the transducer receiving the electronic signal and the magnet mounted at or near the tympanic membrane causes the magnet to vibrate and thus mechanically transmits the sound through the vibration to the ear. Typically, however, the remainder of the hearing aid is inserted into the ear canal or on the outer ear and can cause to the problems discussed above. Still further, the transducers and/or magnets of the hearing aids are mounted in a relatively invasive procedure. For instance, one contact transducer having a magnet is installed by cutting through the tympanic membrane, microscopically drilling bone structure and screwing the magnet to the malleus of the ossicular chain in the middle ear. Such procedures are expensive and can be painful.

Therefore, there remains a need for a relatively compact hearing aid that can be inserted in the ear canal and/or through the tympanic membrane using simplified surgical procedures and that can be hidden from external view.

SUMMARY OF THE INVENTION

The present invention provides an apparatus and method for inserting a relatively compact hearing aid at least partially through the tympanic membrane using a simplified surgical procedure. The hearing aid includes a microphone, an amplifier, and at least one speaker that can be assembled into a single enclosure for insertion through the tympanic membrane. The simplified surgical procedure can be performed on an outpatient basis and generally includes anesthetizing a portion of the tympanic membrane, forming an incision with a cutting instrument in the tympanic membrane and inserting the hearing aid at least partially therethrough. Incisions and placement of a tube in an tympanic membrane for ear drainage is routinely performed in pediatric patients and combines low morbidity and good patient tolerability. The tympanic membrane restrains the hearing aid in position for at least a period of time. A power source, such as a battery, powers the hearing aid. Further, a receiver may be included with the hearing aid and can control the hearing aid from external sources. The receiver can control the amplified volume, receive sound transmissions from the opposite ear or a hearing aid in the opposite ear or receive personal communications.

In one aspect, the invention provides an apparatus for enhancing hearing, comprising a microphone, an amplifier coupled to the microphone, a speaker coupled to the amplifier, the microphone, the amplifier and the speaker being connected to each other and insertable at least partially through a tympanic membrane of a user. In another aspect, the invention provides a method of inserting a hearing aid into an ear comprising inserting a cutting device into an ear, forming an incision in a tympanic membrane, and inserting a hearing aid comprising a microphone, an amplifier and a speaker at least partially through the tympanic membrane.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
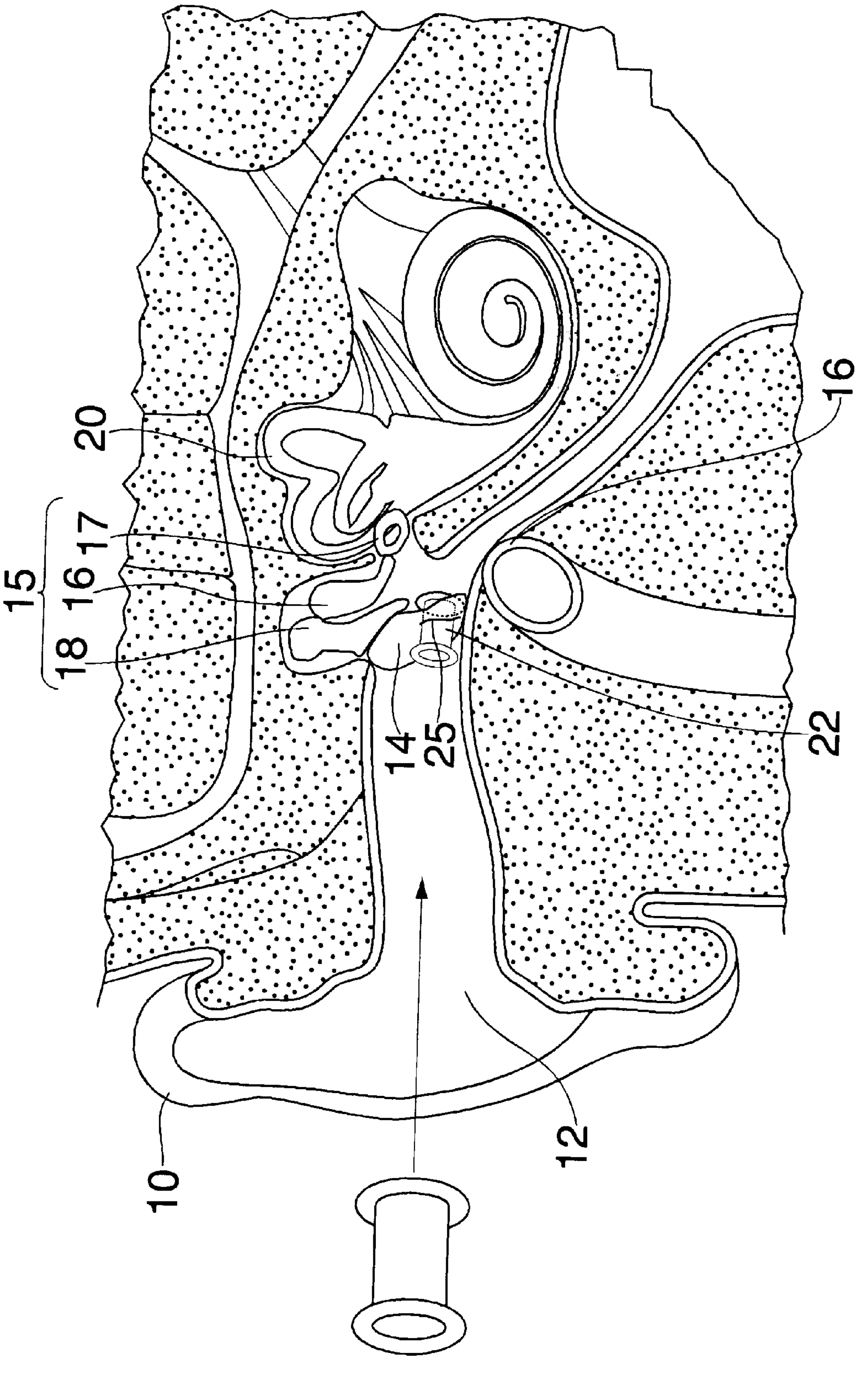
FIG. 1 is a cross-sectional schematic of an car having the hearing aid inserted through the tympanic membrane.

FIG. 1 is a cross-sectional schematic view of a hearing aid inserted through the tympanic membrane in an ear of a user. The ear includes an outer ear 10, an ear canal 12 coupled to the outer ear 10, a tympanic membrane 14 disposed near a distal end of the ear canal 12 from the outer ear 10. An ossicular chain 15, located in a middle ear and disposed on an opposite side of the tympanic membrane 14 from the outer ear 10, couples and amplifies vibrations from the tympanic membrane 14 to an inner ear having a spiral structure known as the cochlea 20. The cochlea 20 converts the vibrations into impulses to the brain. The structure of the outer ear 10 provides a "funnel" to direct and amplify sound waves into the ear canal 12.

The hearing aid 22 of the present invention can be inserted through the outer ear 10 into the ear canal 12 and at least partially through the tympanic membrane 14. The hearing aid 22 includes a microphone, an amplifier coupled to the microphone and at least one speaker, described in more detail below. The hearing aid 22 receives sound waves conducted from the outer ear 10 through the ear canal 12, converts the sound waves into electrical or electromagnetic signals, amplifies the signals and converts the amplified signals into amplified sound waves. The amplified sound waves impact the tympanic membrane 14, and/or portions of the middle and inner ear, and vibrate the ossicular chain 15, specifically the malleus 18, the incus 16 and the stapes 17. These three bones in the ossicular chain 15 act as a set of levers that amplify the vibrations received by the tympanic membrane 14. The stapes 17 is coupled to the entrance of a spiral structure known as the cochlea 20 that contains an inner ear fluid. The mechanical vibrations of stapes 17 causes the fluid to develop fluid impulses that causes small hair-like cells (not shown) in the cochlea 20 to vibrate. The vibrations are transformed into electrical impulses which are transmitted to neuro-pathways in the hearing center of the brain resulting in the perception of sound.

Figure 2:
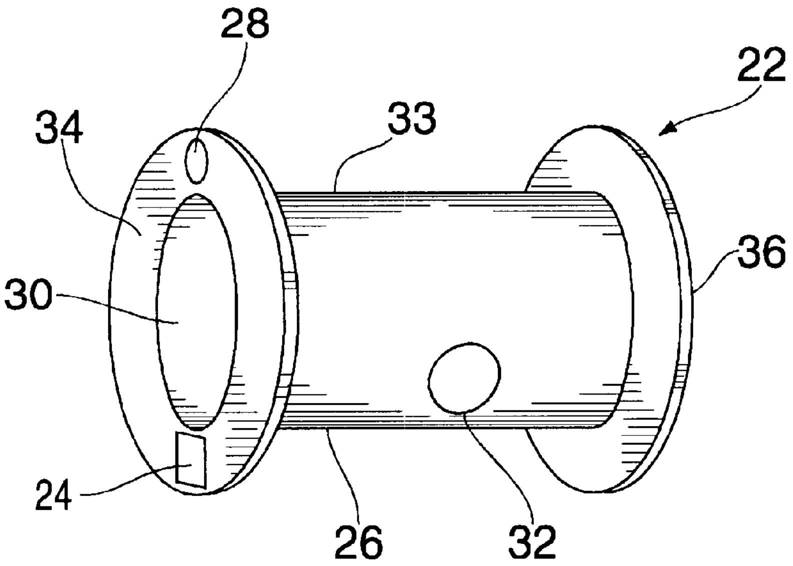
FIG. 2 is a schematic perspective view of the hearing aid.

FIG. 2 is a schematic perspective view of the hearing aid 22. The hearing aid includes a microphone 24, an amplifier 26 coupled to the microphone, at least one speaker 28 coupled to the amplifier and a power source 32, such as a battery. The materials that contact the tissues of the ear are preferably biocompatible, such as silicon, titanium, fluoroplastics or other materials. The microphone 24 converts the sound waves or acoustic energy into electrical or electromagnetic signals. The amplifier 26 amplifies the signals from the microphone to enhance the hearing and hence provide increased hearing capabilities. The speaker 28 reconverts the amplified signals into amplified sound waves and emits the sound waves to the ear. The microphone, amplifier and speaker can be inserted within a tube 33 to form a unitized assembly. Alternatively, the microphone, amplifier and/or speaker can be attached together to form the unitized assembly with adhesives, such as epoxy, or with mating threads or by soldering or welding or other known attachment methods. Alternatively, the microphone, amplifier and speaker may be housed independently and/or move independently of each other to reduce sound alteration or attenuation.

The hearing aid 22 may also include the flanges 34 and 36 disposed along the tube 33. The flanges assist in retaining the hearing aid 22 in the tympanic membrane 14. Typically, the microphone 24 would be placed on the end of the hearing aid 22 facing the outer ear canal 12. The microphone 24 can be located on a flange in the assembly of the hearing aid 22. Similarly, the speaker 28 can be located on a flange in the assembly. The hearing aid 22 can also include a vent hole or vent holes 30 of varying sizes and configurations formed therethrough. The vent hole 30 assists in equalizing pressures between an ear region on each side of the tympanic membrane 14. Other embodiments may not include such vent hole(s). Alternatively, one or both of the flanges can comprise the power source, such as a battery, connected to the other components of the hearing aid 22.

The microphone 24 can be a high sensitivity microphone 24. Preferably, the amplifier 26 can be a high efficiency, high gain amplifier that can amplify the sounds preferably by at least 25 dB and more preferably by at least about 45 dB. The amplifier can be assisted by the natural amplification of the external ear 10 and the ear canal 12. A filter (not shown) can be used to filter noise and can include analog-to-digital and digital-to-analog converters. For example, analog signals from the microphone could be converted to digital signals, where digital signals are less sensitive to noise interference from extraneous transmission sources, such as mobile radio equipment, automobile telephones, and other electromagnetic waves. The digital signals could then be amplified, and the digital signals reconverted to analog signals for output through the speaker.

The hearing aid 22 preferably produces frequency distortions having levels no greater than about 1% at 500 Hz, 1% at 800 Hz and 0% at 1600 Hz and is preferably able to reproduce sounds from about 20 Hz to about 20 kHz. It is believed that the speaker will reduce the inherent attenuation of sound transmitted across air to the tympanic membrane that can occur in other hearing aids, because the speaker is in contact with the membrane itself. The power source 32 may advantageously be a battery, such as a nickel-cadmium or lithium cell type battery. Preferably, the power source 32 would last at least as long as the hearing aid 22 remains inserted through the tympanic membrane 14, typically one to two years. Alternatively, the power source 32 can be a remote power source that supplies energy to the other components of the hearing aid 22 through electromagnetic radiation, such as infrared radiation waves or ultrasonic waves. In such example, the hearing aid 22 could include a remote transmitter (not shown) to transmit the energy and a receiver (not shown) attached to the hearing aid 22 to receive and convert the energy into electrical power for the components. The brands and models for the components described herein are illustrative only. Other brands and/or models may also be used.

Figure 3:
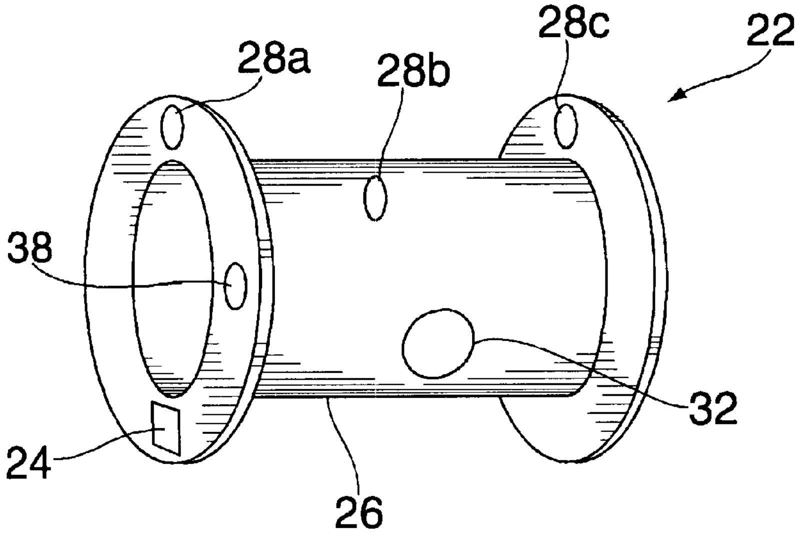
FIG. 3 is a schematic perspective view of an alternative embodiment of the hearing aid.

FIG. 3 is a schematic perspective view of an alternative embodiment of the hearing aid. Similar elements of the embodiments shown in FIGS. 2 and 3 are similarly numbered. The embodiment of FIG. 3 shows a plurality of speakers 28*a–c*. Preferably, the hearing aid 22 is partially inserted through the tympanic membrane 14, shown in FIG. 1. With such a placement, speaker 28*a* would be disposed outwardly toward the ear canal 12. Speaker 28*c* would be disposed inward of the ear canal on the inside of the tympanic membrane 14 and toward the ossicular chain 15 of the middle ear. It is believed that the speaker 28*c* may provide additional impulses in the middle ear and toward the cochlea 20 through a window in the cochlea. A middle speaker 28*b* can be disposed between speakers 28*a* and 28*c* for additional sound output on either side of the tympanic membrane, depending on the intersection of the hearing aid 22 with the tympanic membrane 14.

The hearing aid 22 may also include a receiver 38. The receiver 38 may be a frequency modulation (FM), amplitude modulation (AM) receiver, ultrasound receiver or other types of receivers and can have several functions. First, the receiver can be used to remotely control the components of the hearing aid 22, such as the amplifier 26. A remote transmitter can provide output signals to be received by the receiver 38 and adjust, for example, the amplification to avoid under or over-amplification of the converted audio signal from the microphone 24. Additionally, the receiver can be used to receive transmissions from an opposite ear or from a hearing aid device in the opposite ear. The receiver can also be used to receive personal communications transmitted to the user. For instance, radio broadcasts, personal voice massaging, and other custom input can be transmitted to the receiver 38 to be amplified and then output through the speakers 28*a–c*.

Figure 4:
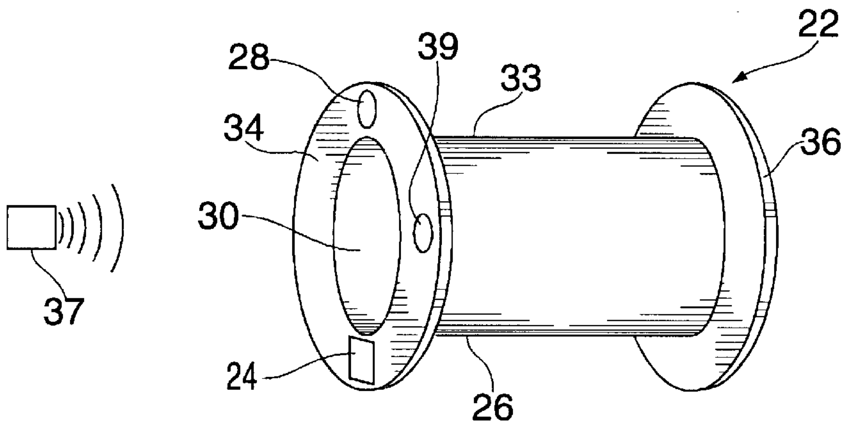
FIG. 4 is a schematic perspective view of an alternative embodiment of the hearing aid.

FIG. 4 is a schematic perspective view of an alternative embodiment of the hearing aid. Similar elements of the embodiments shown in FIGS. 2, 3 and 4 are similarly numbered. The hearing aid can be powered from a remote power source that supplies energy to the amplifier and other components of the hearing aid 22 through electromagnetic radiation, such as infrared waves. In such example, the hearing aid 22 would include a remote transmitter 37 to transmit the energy and a receiver 39 coupled to the hearing aid 22 to receive the energy and convert the energy into electrical power for the various components.

Figure 5:
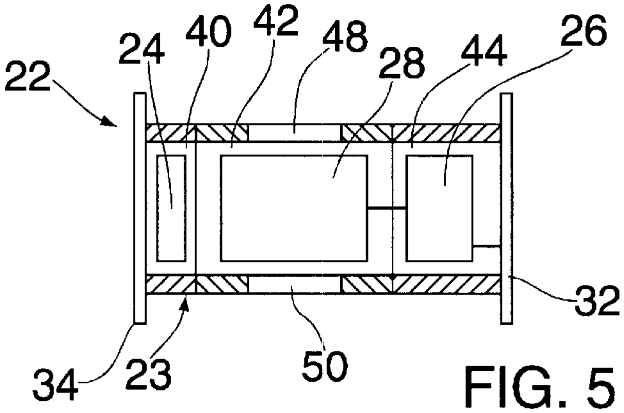
FIG. 5 is a schematic cross sectional view of an alternative embodiment of the hearing aid.

FIG. 5 is a schematic cross sectional view of an alternative embodiment of the hearing aid. Similar elements of the embodiments as shown in FIGS. 2, 3, 4 and 5 are similarly numbered. The hearing aid 22 can be assembled into a unit 23 that resists vibrational effects resulting from the movement of the tympanic membrane on at least one member of the components including the microphone 24, amplifier 26 and speaker 28. It is believed that such an arrangement may reduce sound distortion or attenuation caused by the relative movement of the components with the tympanic membrane to which the hearing aid is coupled, similar to the well known Doppler effect that causes an apparent change in the frequency of waves from relative motion between a sound source and a sound receiver. FIG. 5 provides one exemplary embodiment of a vibration dampening unit.

A flange 34 is coupled to a chamber 40 that houses a microphone 24. The chamber 40 is coupled to a chamber 42 that houses a speaker 28. The chamber 42 is coupled to a chamber 44 that houses an amplifier 26. The chamber 44 is coupled to a power source 32, such as a battery. The microphone 24 is electrically coupled to the amplifier 26 and the amplifier 26 is electrically coupled to the speaker 28 and to the power source 32. One or more sound transmissive windows 48, 50 are coupled to the chamber 42 and allow the sound waves from the speaker 28 to be transmitted through the chamber 42 to the tympanic membrane, shown in FIG. 1. One or more of the chambers 40, 42 and 44 can be at least partially filled with a fluid. It is believed that the mass of the fluid and the resulting inertia of the components within the fluid can reduce the motion of the components relative to incoming sound waves to the microphone and/or outgoing sound waves from the speaker. Other vibration dampening effects are possible, such as use of elastic compounds instead of fluids, air suspension, gyroscopic inertia forces on components produced by rotating the components rapidly, and the other methods known to those in the art.

Figure 6:
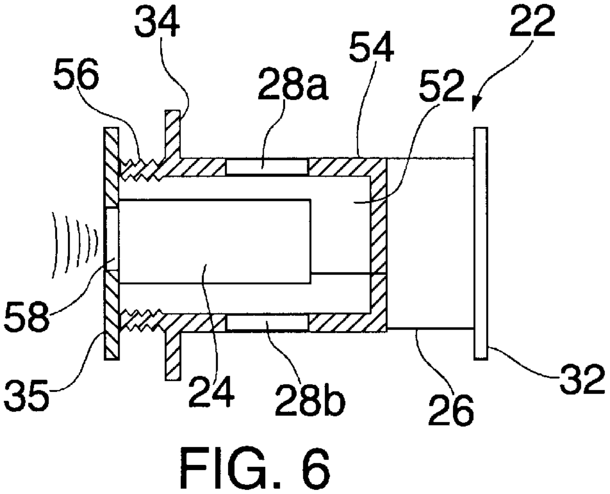
FIG. 6 is a schematic cross sectional view of an alternative embodiment of the hearing aid.

FIG. 6 is a schematic partial cross sectional view of another embodiment of the hearing aid. The hearing aid 22 includes elements previously described in reference to FIGS. 2–5 and further includes a chamber 52 for vibrational dampening, similar to the vibrational dampening aspects described in reference to FIG. 5. A flange 35 is coupled to a microphone 24. An outer shell 54 is disposed around the microphone 24, forming a chamber 52 that contains a fluid therebetween. The outer shell 54 is coupled to a flange 34. The flange 34 is flexibly coupled to the flange 35 by a flexible coupling 56 that is used to retain the fluid within the chamber 52. One or more openings 58 formed in the flange 35 allow sound waves to be received by the microphone 24. The outer shell 54 is coupled to an amplifier 26 disposed either within the outer shell or adjacent the outer shell. A power source 32, such as a battery, is coupled to the amplifier 26. The amplifier 26 is coupled to one or more speakers 28*a–b*. The speakers 28*a–b* can be disposed on the outer shell 54. Alternatively, the speakers can be disposed within the outer shell and can transmit sound through an acoustically transparent medium, such as shown in FIG. 5, to the outside of the shell.

Figure 7:
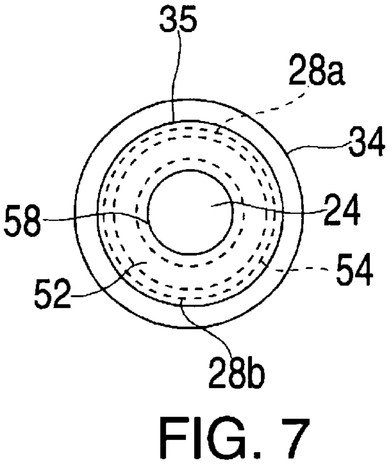
FIG. 7 is a schematic end view of the embodiment shown in FIG. 6.

FIG. 7 is a schematic end view of the embodiment shown in FIG. 6. A flange 35 is coupled to a flange 34. The flange 34 is coupled to an outer shell 54. The outer shell preferably supports speakers 28*a–b*. A microphone 24 is disposed radially inward of the outer shell 54 in a chamber 52. Preferably, the flange 35 has one or more openings 58 through which sound waves may be received by the microphone 24.

Referring to FIG. 1, the hearing aid 22 can be inserted at least partially through the tympanic membrane 14 with a relatively unobtrusive surgical procedure. One exemplary procedure would include anesthetizing a portion of the membrane by inserting a drop of phenol or other fluids on the tympanic membrane 14. Alternatively, the tympanic membrane 14 can be anesthetized by injecting a localized anesthetic, such as lidocaine, into the tissues of the ear canal 12. A tubular instrument (not shown) is inserted into the ear canal 12, such as an ear speculum, to view the tympanic membrane and to provide a safe conduit for a cutting instrument. In conjunction with an operating microscope, the cutting instrument is inserted through the ear speculum and forms a small slit 25 in the tympanic membrane 14. The cutting instrument may be a knife, a laser, an ultrasonic transducer, and other cutting devices. The small incision can be done in a physician's office or on an out-patient basis with generally minimal difficulty. After the slit 24 is formed in the tympanic membrane 14, the hearing aid 22 is inserted through the ear canal 12 and at least partially through the slit 24. Preferably, the hearing aid 22 is inserted through the tympanic membrane 14 so that a portion of the hearing aid extends into the ear canal 12. The tympanic membrane 14 restrains the hearing aid 22 from becoming dislodged into the ear canal 12. A portion of the hearing aid 22 that extends into the ear canal 12 provides a surface through which the microphone 24, shown in FIGS. 2–7, can receive input of sound waves through the ear canal 12. Typically, the tympanic membrane will grow and heal around the hearing aid 22. In an extended period of time, such as one to two years, the tympanic membrane 14 may press the hearing aid 22 out of the membrane. Further, the hearing aid 22 may be secured to the tympanic membrane 14, to a ring on the tympanic membrane (not shown), known as a tympanic membrane annulus, or to the ear canal 12. Due to the relatively noninvasive and simplified procedure, the hearing aid 22 can be discarded and a new hearing aid inserted in much the same manner with a new battery to last for the next period of time in which the hearing aid 22 remains secured in the tympanic membrane 14. Alternatively, the same hearing may be re-inserted easily in the office with a new battery or power source.

While foregoing is directed to the preferred embodiment of the present invention, other and further embodiments of the invention may be devised without departing from the basic scope thereof, and the scope thereof is determined by the claims that follow. For instance, the receivers can be combined into the various embodiments. The vibration dampening aspects described can be applied to any or all of the components. Further, the sequence of assembly can be varied, for example, by placing the speaker and receiver adjacent each other and the amplifier adjacent a power source. Thus, it is understood that the various components that coupled to each other can be connected indirectly or directly to each other.

What is claimed is:

1. An apparatus for enhancing hearing, which apparatus is insertable at least partially through a tympanic membrane of a user, comprising:

a) a microphone;

b) an amplifier coupled to the microphone;

c) a speaker coupled to the amplifier, the microphone, the amplifier and the speaker being connected to each other into a single unit.

2. The apparatus of claim 1, further comprising a receiver electrically coupled to the amplifier.

3. The apparatus of claim 2, wherein the receiver comprises a frequency modulated receiver.

4. The apparatus of claim 2, wherein the receiver is tunable from a remote location.

5. The apparatus of claim 1, wherein the apparatus further comprises a means for retaining the single unit in the tympanic membrane.

6. The apparatus of claim 1, wherein the apparatus is powered by electromagnetic radiation.

7. The apparatus of claim 6, wherein the electromagnetic radiation is an infrared source.

8. The apparatus of claim 1, further comprising a plurality of speakers coupled to the amplifier.

9. The apparatus of claim 8, wherein at least one of the speakers is adapted to be external to the tympanic membrane and at least one of the speakers is adapted to be internal to the tympanic membrane.

10. The apparatus of claim 1, wherein the apparatus comprises one or more vent holes disposed therethrough.

11. The apparatus of claim 1, further comprising a housing into which at least one component of the microphone, amplifier and speaker components is disposed that dampens vibrational movement.

12. A method of inserting a hearing aid into an ear, comprising:

a) inserting a cutting device into an ear;

b) forming an incision in a tympanic membrane;

c) inserting a hearing aid comprising a microphone, an amplifier and a speaker as a unit at least partially through the tympanic membrane.

13. The method of claim 12, further comprising allowing the tympanic membrane to restrain the hearing aid after insertion.

14. The method of claim 12, further comprising controlling the performance of the hearing aid with a receiver mounted with the microphone, the amplifier and the speaker.

15. The method of claim 14, wherein the receiver is controlled from a remote location.

16. The method of claim 12, wherein the hearing aid has a ventilation hole.

17. The method of claim 12, further comprising a) providing a plurality of speakers coupled to the amplifier; and b) positioning the hearing aid so that at least one speaker is adapted to be external to the tympanic membrane and at least one speaker is adapted to be internal to the tympanic membrane.

18. The method of claim 12, further comprising placing the hearing aid in the ear in a position that does not obstruct the outer ear or the ear canal.

19. The method of claim 18, wherein the placing of the hearing aid allows natural sound transmissions from an external source through the outer ear and ear canal to be amplified by the outer ear and ear canal to the hearing aid that is inserted at least partially through the tympanic membrane.

20. The method of claim 12, further comprising allowing the receipt of transmissions external to the ear through a receiver coupled to the hearing aid.

21. The method of claim 12, further comprising allowing the receipt of transmissions through a receiver coupled to the hearing aid from a second hearing aid in an opposite ear.

22. An apparatus for enhancing hearing, comprising:

a) an outer shell comprising at least two flanges;

b) a microphone;

c) an amplifier; and d) a speaker;

the microphone, the amplifier and the speaker being coupled to the outer shell and electrically coupled to each other.

23. The apparatus of claim 22, further comprising a receiver coupled to the outer shell.

24. An apparatus for enhancing hearing, comprising:

a) a tube comprising two flanges;

b) a microphone connected to the tube;

c) an amplifier connected to the tube and coupled to the microphone; and d) a speaker connected to the tube and coupled to the amplifier.

25. The apparatus of claim 24, further comprising a plurality of speakers connected to the tube and coupled to the amplifier.

26. The apparatus of claim 25, wherein one of the speakers is connected to one of the flanges and another of the speakers is connected to another one of the flanges.

27. The apparatus of claim 24, further comprising a receiver coupled to the tube.

* * * * *

UNITED STATES PATENT AND TRADEMARK OFFICE

CERTIFICATE OF CORRECTION

PATENT NO. : 6,386,633 B1 
DATED : May 14, 2002
INVENTOR(S) : Newton

It is certified that error appears in the above-identified patent and that said Letters Patent is hereby corrected as shown below:

Column 4,
Line 30, "seat-sell" should read -- seat-shell --.

Column 5,
Line 4, "sea" should read -- seat --;
Line 32, "clawed" should read -- claimed --.

Column 6,
Line 26, "font" should read -- front --.

Signed and Sealed this

Twenty-third Day of July, 2002

*Attest:*

JAMES E. ROGAN

*Attesting Officer* *Director of the United States Patent and Trademark Office*